United States Patent [19]
Bilof et al.

[11] Patent Number: 5,755,713
[45] Date of Patent: May 26, 1998

[54] LAPAROSCOPIC INSTRUMENT ASSEMBLY INCLUDING A PLURALITY OF INSTRUMENTS

[76] Inventors: Michael L. Bilof, 2 Karam Cir.; Michael J. Nusbaum, 17 Cadmus Ct., both of West Orange, N.J. 07052

[21] Appl. No.: 660,160

[22] Filed: Jun. 3, 1996

[51] Int. Cl.[6] .................................................. A61B 17/00
[52] U.S. Cl. ........................ 606/1; 606/205; 600/104
[58] Field of Search ...................... 606/1, 205; 600/104, 600/106

[56] References Cited

U.S. PATENT DOCUMENTS

| | | |
|---|---|---|
| 4,686,965 | 8/1987 | Bonnet et al. ........................... 600/104 |
| 5,234,443 | 8/1993 | Phan et al. . |
| 5,261,917 | 11/1993 | Hasson et al. . |
| 5,312,391 | 5/1994 | Wilk . |
| 5,395,369 | 3/1995 | McBrayer et al. . |

Primary Examiner—Michael H. Thaler
Attorney, Agent, or Firm—Curtis, Morris & Safford, P.C.; Matthew K. Ryan; David Rubin

[57] ABSTRACT

A laparoscopic instrument assembly with a rigid outer housing, housing multiple guide disks. The guide disks rotate inside the instrument assembly 360 degrees around a center post and guide the rotation, positioning, and implementation of multiple laparoscopic instruments. A plurality of laparoscopic instruments are rotated into position utilizing a selector knob attached to said center post. Once properly positioned, the selected laparoscopic instrument is axially translated into the forward position where it couples to an actuating handpiece. The actuating handpiece engages the selected laparoscopic instrument by pivoting from its disengaged position about a pivot point, thus allowing use of the selected laparoscopic instrument. The instrument can be thus be withdrawn and another instrument selected in the same manner.

11 Claims, 12 Drawing Sheets

LAPAROSCOPIC INSTRUMENT ASSEMBLY INCLUDING A PLURALITY OF INSTRUMENTS

FIELD OF THE INVENTION

The present invention relates to a laparoscopic instrument assembly and more broadly to method for facilitating the performance of laparoscopic surgery.

BACKGROUND OF THE INVENTION

Laparoscopic surgery has existed for several decades. Indeed, rudimentary forms were in evidence at the beginning of this century. Its current state of popularity can be traced to initial published reports of laparoscopic cholecystectomy (removal of the gallbladder) in the 1980's. Prior to this cholecystectomy involved a sizeable abdominal incision. Hospitalization was from 5-10 days and the total convalescence was typically 4-6 weeks. With current laparoscopic techniques most patients will be discharged from the hospital within 24 hours and will resume full activities within 4-7 days. Cost savings from decreased hospitalization and recovery time are substantial.

Laparoscopy generally entails piercing the abdominal wall through small 2-5 centimeter incisions. After the initial perforation the abdominal cavity is generally pressurized with carbon dioxide gas to a pressure of 12-15 centimeters water pressure. Once sufficient pressure is generated the desired number of perforations are made for the given procedure. Through these perforations are introduced various laparoscopic tubular ports, known as cannulas or trocars, and into these ports are place the appropriate laparoscopic instruments. Currently, one laparoscopic instrument at a time is placed into each port. During the course of a typical laparoscopic procedure multiple instruments will be required. When this situation arises either another perforation with a trocar is needed for introduction of the required instrument, or the currently used instrument is removed allowing introduction of the needed instrument into the same trocar. These motions can be cumbersome and awkward resulting in increased operating times, as well as the potential for contamination of the operative field.

Recently, as surgeons have become more adept with laparoscopic instrumentation and techniques, the scope of procedures which can be performed using laparoscopy has dramatically increased. Accordingly, as the complexity of the procedures escalates the need for increasing numbers of instruments per procedure has risen. Thus, the need for a device which allows for a rapid and smooth transition between laparoscopic instruments during a surgical procedure has been found to be desirable.

OBJECTS OF THE INVENTION

An object of the present invention is to provide a laparoscopic instrument assembly for increased efficiency in the performance of laparoscopic surgery.

A more particular object of the invention is to provide a laparoscopic instrument assembly in which are simultaneously housed multiple laparoscopic instruments.

A further object of the invention is to provide a device which allows individual use of multiple laparoscopic instruments without the need for moving presently unused instruments extracorporeally.

Another object of the invention is to allow uncoupling of the presently used laparoscopic instrument from the actuating handpiece and engagement with another laparoscopic instrument by the actuating handpiece without the need for removing either component from the laparoscopic instrument assembly.

Another object of the invention is to provide a laparoscopic instrument assembly in which one or more laparoscopic instruments may be removed from or added to the assembly, before, during or after surgery.

Another object of the invention is to provide an actuating instrument which allows for rotational motion of a laparoscopic instrument.

Another object of the invention is to provide an actuating handpiece which allows for rotational motion of a laparoscopic instrument via a rotating knob and system of intervening gears wherein that system can be operated with the same hand which is operating the actuating handpiece and without the need for the surgeon to remove his hand from the actuating handpiece.

Another object of the invention is to provide a removable rear plate assembly for a laparoscopic instrument which permits use of a device by allowing it to pass through the body of the rear plate while allowing said device to move freely within the housing and to be connected to an external piece of equipment.

Various other objects, advantages and feature of the present invention will become readily apparent from the ensuing detailed description and the novel features will be particularly pointed out in the appended claims.

SUMMARY OF THE INVENTION

In accordance with the present invention, a laparoscopic instrument assembly comprises a rigid tubular outer housing within which are housed a plurality of slidably mounted laparoscopic instruments. The outer diameter of the laparoscopic instrument assembly is smaller than the inner diameter of a laparoscopic cannula or trocar thereby allowing insertion of the entire width of the assembly inside of the body of a patient through the cannula.

According to the present invention, a single laparoscopic instrument assembly is provided which allows for housing of multiple laparoscopic instruments. This instrument assembly is then inserted through a single laparoscopic trocar sleeve or cannula.

According to another feature of the present invention, a plurality of laparoscopic instruments are introduced into the instrument housing assembly through the proximal end of the housing by removing a rear plate assembly and a positioning knob. A further embodiment of the present invention is that the aforementioned laparoscopic instruments are held in place by several rotating guide disks within the assembly. The guide disks are fixed to a center post as one unit which can be removed from the housing if needed.

A further feature of the present invention is that the center post is releasably attached to a selector knob which facilitates positioning. This selector knob allows for the rotational motion around the center post by the guide disks.

A further embodiment of the present invention is that the guide disks allow for the rotation, and implementation of the laparoscopic instruments. Utilizing the selector knob, the guide disks will guide the selected instrument to the proper position for coupling with the actuating handpiece.

An additional feature of the invention is that once the selected instrument is positioned rotationally (to allow coupling with the actuating handpiece), it is axially translated distally to its advanced position; and in so doing it exits the instrument assembly at the distal end of the housing by pushing a distal flap valve into an open position. In this advanced position the actuating handpiece may engage the instrument thus allowing for use of that instrument. The slidability of the instruments relative to the housing and the guideposts allows for coupling between the selected instrument and the actuating handpiece and thus the use of the instrument.

The present invention also includes an advantageous actuating handpiece which is mounted to the housing. The handpiece is movable between two positions, namely, an engaged position and a disengaged position. While in the disengaged position, the actuating handpiece is positioned, relative to the housing, in such a manner as to allow for the axial translation distally of the selected laparoscopic instrument. Once the selected instrument is properly positioned for coupling with the actuating handpiece, the handpiece can be rotated about its pivot point and swing arm into the engaged position, allowing an operator to actuate the selected instrument.

A further embodiment of the actuating handpiece includes an instrument rotating knob which comprises a rotating wheel attached to several intervening gears within the body of the handpiece which, in turn, mesh with a gear on the currently selected instrument. The purpose of the gear is to allow for rotational motion of the operating laparoscopic instrument. Thus, while the surgeon is manipulating the handpiece, he or she may cause rotational motion of the selected laparoscopic instrument without the need to remove his or her hand from the handpiece.

Once an operator has completed using the laparoscopic instrument assembly, the actuating handpiece is uncoupled from the instrument and rotated to the disengaged position. The instrument can then be axially translated proximally, and once this is accomplished, another instrument can be selected by utilizing the selector knob.

The operative laparoscopic instruments which may be placed inside the instrument assembly include, but are not limited to scissors, forceps, dissectors, graspers, suture applicators, suction and irrigation devices.

Further features of the present invention are the rear plate assembly which is releasably attached to the proximal end of the housing, and the selector knob which is releasably attached to the proximal end of the center post. The rear plate assembly includes an outer disk and an inner disk. The outer disk which attaches to the housing in a fixed position thus providing the orientation for the entire instrument. This orientation is provided by means of its fixed relationship to the housing assembly and the indexing grooves of the outer disk. The inner disk has a center hole which provides an exit for the center post, and a more peripheral instrument extension hole which is aligned with one of the sets of holes in the guide disks. (Guide disks are described at FIG. 3 and the discussion relating thereto, infra). This peripheral hole allows for external access to a device within the housing which may then be connected to external equipment. The inner disk also has several other holes which are spaced to facilitate the placement of screws rigidly connecting it to the instrument selector knob. The inner disk is freely rotatable within the outer disk. The rear plate assembly is mounted over the center post onto the housing. The selector knob is positioned on the center post. The center post has two slots cut into it at 180 degrees from each other. These slots provide the articulation points for a locking tab on the selector knob. Once this articulation has been accomplished, the proper orientation of the instrument with respect to the selector knob is assured. Spring loaded ball bearings on the selector knob can now engage the indexing notches on the fixed outer disk of the rear plate assembly. Thus, when the ball bearings engage the indexing notches, an operating surgeon knows that one of the laparoscopic instruments within the housing is properly positioned to slide forward for coupling with the actuating handpiece.

A laparoscopic instrument assembly in accordance with the present invention will vastly improve the facility with which an operator can perform laparoscopic surgery. The present invention allows for the use of a greater number of laparoscopic instruments per trocar site and additionally greater efficiency in their use. The facility of laparoscopic surgery is increased in that a plurality of instruments are provided within a single housing, and thus obviate the previous need to remove instruments from the abdomen or provide new trocar sites in order to introduce new instruments.

BRIEF DESCRIPTION OF THE INVENTION

The following detailed description, given by way of example, will best be understood in conjunction with the accompanying drawings in which:

FIG. 12 is an enlarged transparent view of the large handle section of the actuating handpiece of FIG. 11(a).

FIG. 13 is a top view of a preferred embodiment of a rotating knob gear assembly for the laparoscopic instrument assembly of FIGS. 1(a)–(c), shown articulated with instrument gear grooves.

FIG. 14 is a side view of a portion of the actuating handpiece articulated with a laparoscopic instrument.

DETAILED DESCRIPTION OF A PREFERRED EMBODIMENT

Figure 1A:
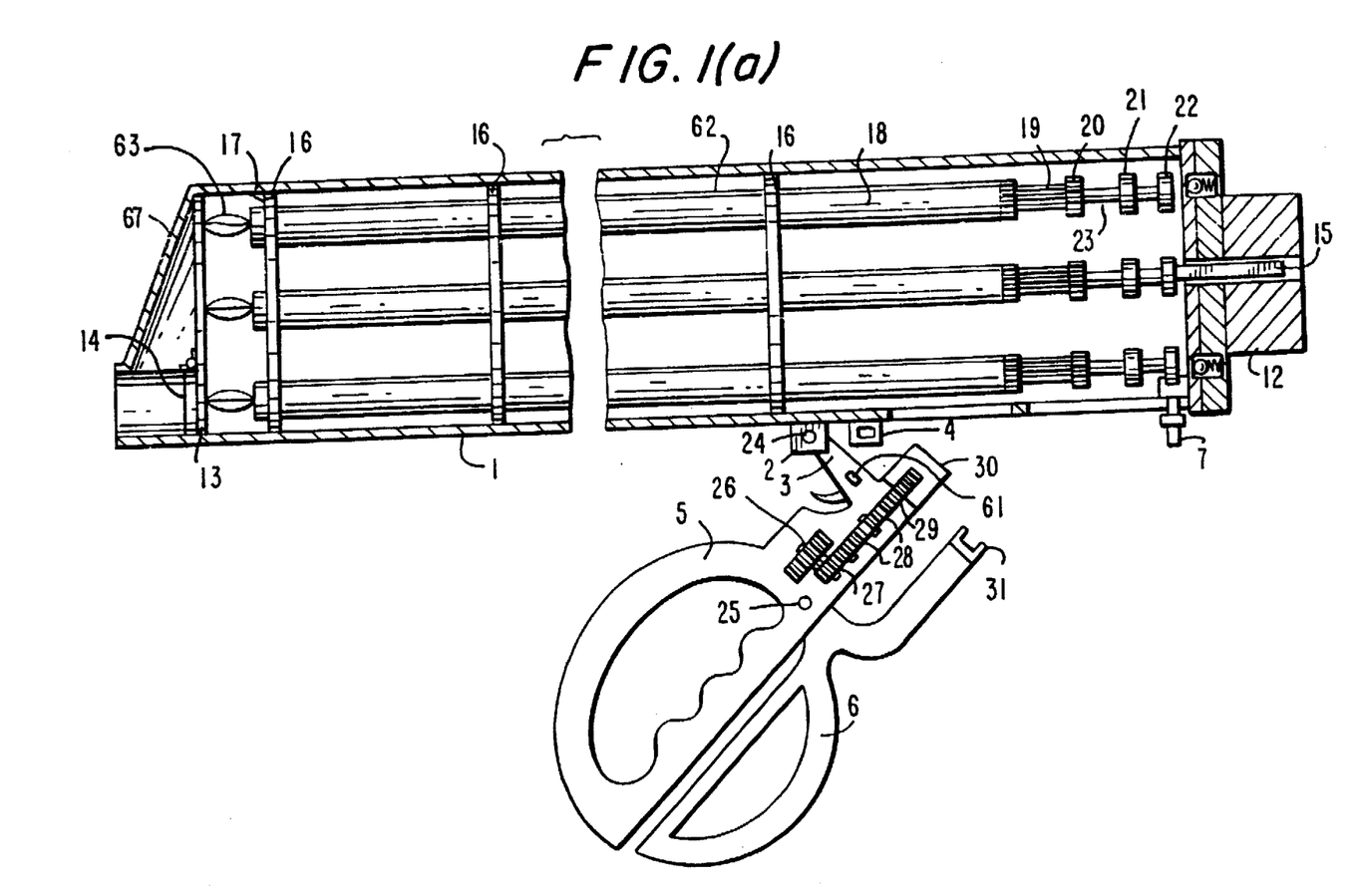
FIG. 1(a) is a side cross sectional view of a preferred embodiment of a laparoscopic instrument assembly in accordance with the teachings of the present invention with handle disengaged, instrument retracted and slider handle in retracted position.
Figure 1B:
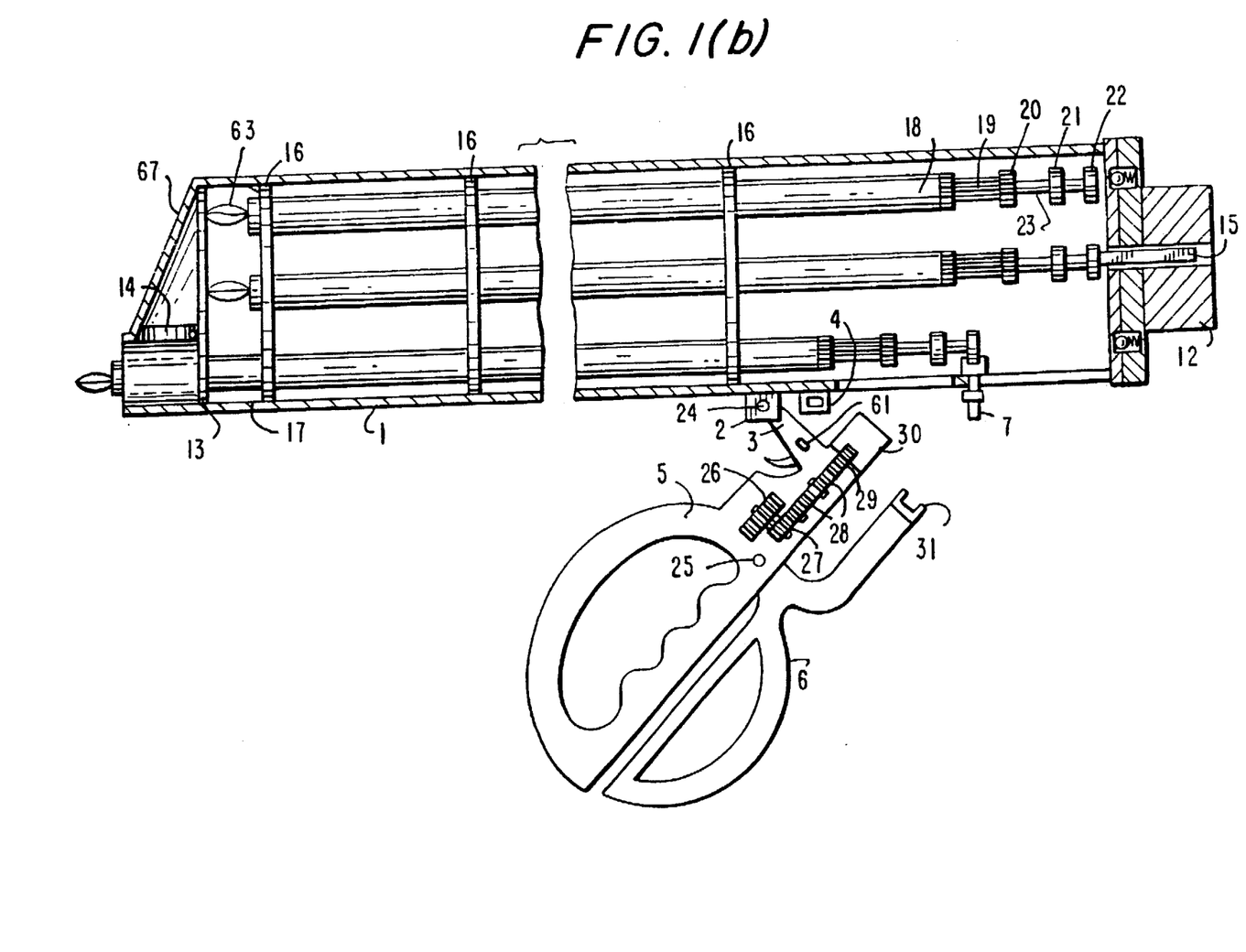
FIG. 1(b) is a side cross sectional view of the laparoscopic instrument assembly of FIG. 1(a) with handle disengaged, instrument advanced and slider handle in advanced position
Figure 1C:
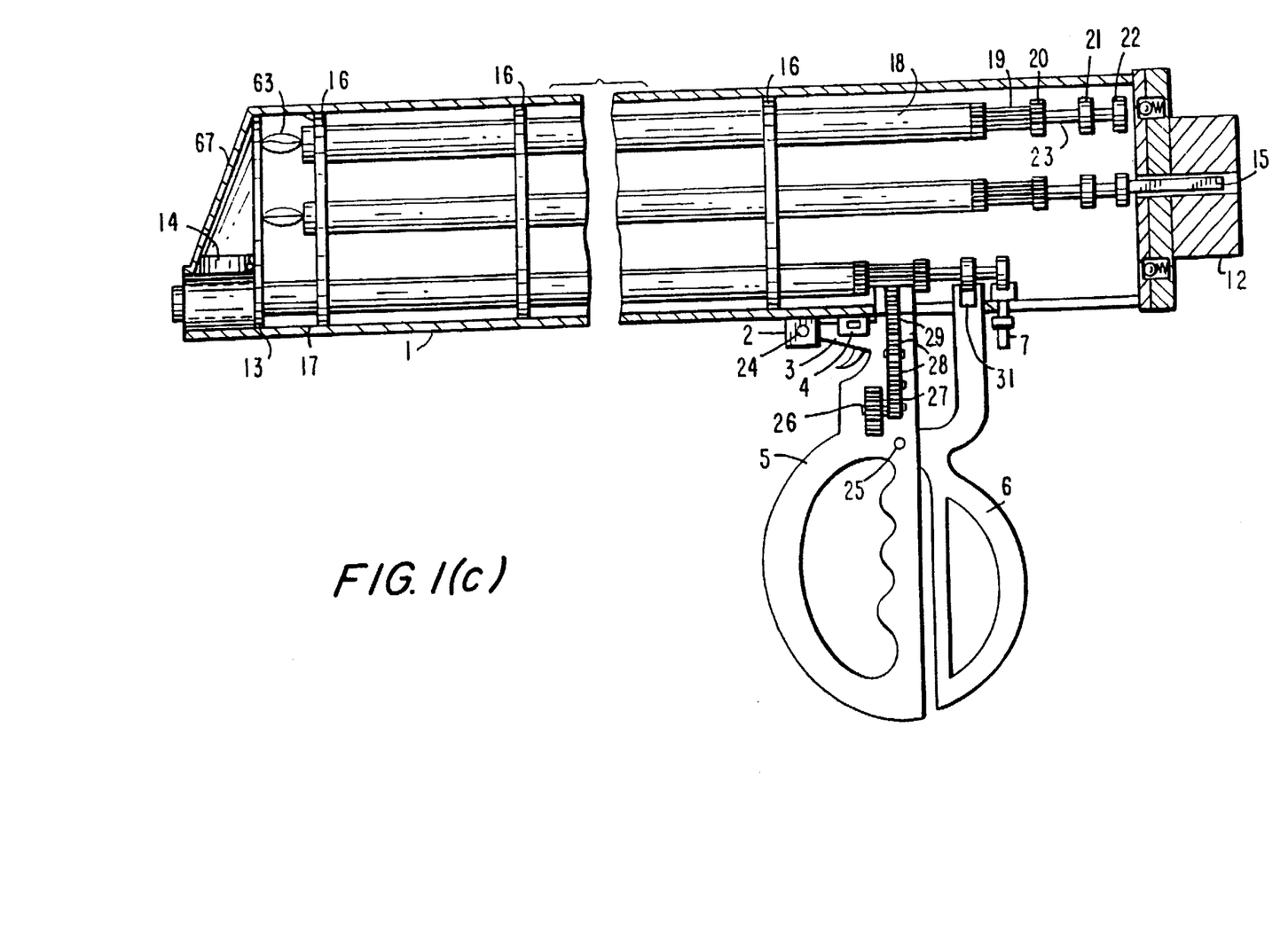
FIG. 1(c) is a side cross sectional view of the laparoscopic instrument assembly of FIGS. 1(a) and (b) with handle engaged, instrument advanced and slider handle in advanced position.

Referring now to the drawings, wherein the like reference numerals are used throughout and in particular to FIGS. 1(a), 1(b) and 1(c), there is illustrated a preferred embodiment of a laparoscopic instrument assembly in three operational states in accordance with the present invention. As is illustrated in FIGS. 1(a)–(c) generally, the laparoscopic instrument assembly comprises a rigid housing 1 and a plurality of laparoscopic instruments 18, each of the instruments comprising an outer shaft 62, an inner shaft 23, instrument gear grooves 19, a gear disk 20, an articulating disk 21 and a surgical tip 63 situated within housing 1. The instruments 18 are mounted within housing 1 on guide disk assembly 66 (shown at FIG. 3(a)) which includes guide disks 16 which are spaced apart and held in position relative to one another by attachment to a center post 15 (shown at FIG. 3(a)). The guide disk assembly 66 sits within the housing 1 and is maintained in its proper position relative to the housing 1 by the guide disk stopper 17 which is attached to or incorporated into the distal inside surface of housing 1 (guide disk stopper 17 is explained in greater detail at the discussion relating to FIG. 3, infra.). Housing 1 has an outer diameter smaller than the inner diameter of a laparoscopic cannula or trocar sleeve, allowing the entire laparoscopic instrument assembly to be inserted in a patient's abdomen through the laparoscopic cannula or trocar sleeve. Insertion into the patient's abdomen is accomplished in the usual fashion known to those skilled in the art. Upon initial insertion of the instrument assembly through the laparoscopic cannula into the abdomen, laparoscopic instruments 18 are fully retracted as illustrated in FIG. 1(a).

FIGS. 1(a)–(c) also illustrate a preferred embodiment of an actuating handpiece for this laparoscopic instrument. The handpiece may be in the disengaged position as shown in FIGS. 1(a) or 1(b), or in the engaged position as shown in FIG. 1(c). The handpiece must be in the disengaged position while the selected laparoscopic instrument 18 is moved to the advanced position along slider track 9 (see discussion relating to FIG. 2, infra).

As shown in FIGS. 1(a)–(c), the actuating handpiece includes a first handle 6 and a second handle 5 which is larger than the first handle. The second handle 5 is pivotally fixed relative to the first handle 6 at instrument handle pivot 25. A further embodiment of the actuating handpiece includes an instrument rotating knob 26 which allows rotation of the selected laparoscopic instrument 18 about its longitudinal axis as follows: Instruments 18 include instrument gear grooves 19 near their proximal ends. When the handpiece is engaged, the instrument rotating knob 26 has a mechanical linkage to the instrument gear grooves 19 of selected laparoscopic instrument 18 via a system of intervening gears 28 with the final number of intervening gears varying with the size of the second handle 5. Rotating knob 26 includes an instrument rotating knob gear 27 which engages one of the intervening gears 28. One of the intervening gears engages articulating gear 29, which, in turn, meshes directly with the instrument gear grooves 19 of selected laparoscopic instrument 18 (see discussion relating to FIGS. 11–14, infra). Thus, while the surgeon is operating the handpiece, the surgeon may, without removing his hand from the handpiece and while continuing to operate the handpiece, rotate selected the laparoscopic instrument 18 360° in either direction via instrument rotating knob 26. As a result thereof, the instrument rotating knob 26 may be operated by either the thumb or index finger of the hand which is operating the actuating handpiece.

As shown in FIGS. 1(a)–(c), the actuating handpiece is pivotably coupled to the outside of housing 1 via handle post 2 and swing arm 3. While the selected laparoscopic instrument 18 is advanced distally along slider track 9 (see FIG. 2 and related discussion, infra) by slider handle 7 the handpiece will generally be in a disengaged position, that is, hanging freely via handle post 2 as shown in FIGS. 1(a)–(b). Once the selected instrument 18 is fully advanced the actuating handpiece is rotated upward by about instrument handle pivot point 24 (shown only in FIG. 1(c)) on handle post 2, to which it is connected via a swing arm 3. Once the actuating handpiece is fully rotated upward toward the proximal end of housing 1 the locking blocks 61 housed within swing arm 3 engage a swing arm catch plate 4 allowing the handpiece to remain in the engaged position without active support from the operating surgeon. As described above, the second handle 5 will engage the selected instrument 18 at instrument gear grooves 19, allowing the instrument rotating knob 26 to articulate with the selected instrument 18 via intervening gears 28 if the surgeon should so desire. Second handle guide 30 (shown only in FIGS. 1(a) and 1(b)) on the apical portion of the second handle 5 ensures proper articulation of the second handle 5 with the gear disk 20. In a similar fashion, first handle articulation guides 31 on the apical portion of the first handle 6 ensure proper articulation with selected instrument 18 at its articulating disk 21. Movement of the second handle 5 relative to the first handle 6 thereby effects movement of the gear disk 20 relative to articulating disk 21.

FIGS. 1(a)–(c) also depict a front plate 13, a valve plate 14, and a valve cap 67, referred to herein collectively as the front plate assembly. The front plate assembly is positioned at the distal end of the housing 1 forming an airtight barrier between the patient and the inside of the housing 1. Front plate 13 is in the form of a disk having an instrument port valve 64 (shown in FIG. 10) through which the selected laparoscopic instruments 18 may be advanced and retracted during a surgical procedure. Because maintenance of the surgical pneumoperitoneum is necessary during a laparoscopic procedure, the instrument port valve 64 is equipped with two airtight members. When the selected laparoscopic instrument 18 is in the retracted position, valve plate 14, to which is attached a valve stopper 37 (shown in FIG. 9), is held in place over the instrument port valve 64 by a valve plate spring 36, which in turn is held in place by a spring plate 65. When the selected laparoscopic instrument 18 is in the advanced position and valve plate 14 is thereby pushed to a "ready" position which does not contribute to airtightness, front plate valve membrane forms an airtight seal between the selected laparoscopic instrument 18 and the instrument port valve 64 (see also, FIG. 10(c)). Valve cap 67 is positioned distal to the front plate assembly and forms a protective barrier between the patient and the mechanical components of the front plate assembly.

Figures 8, 9A:
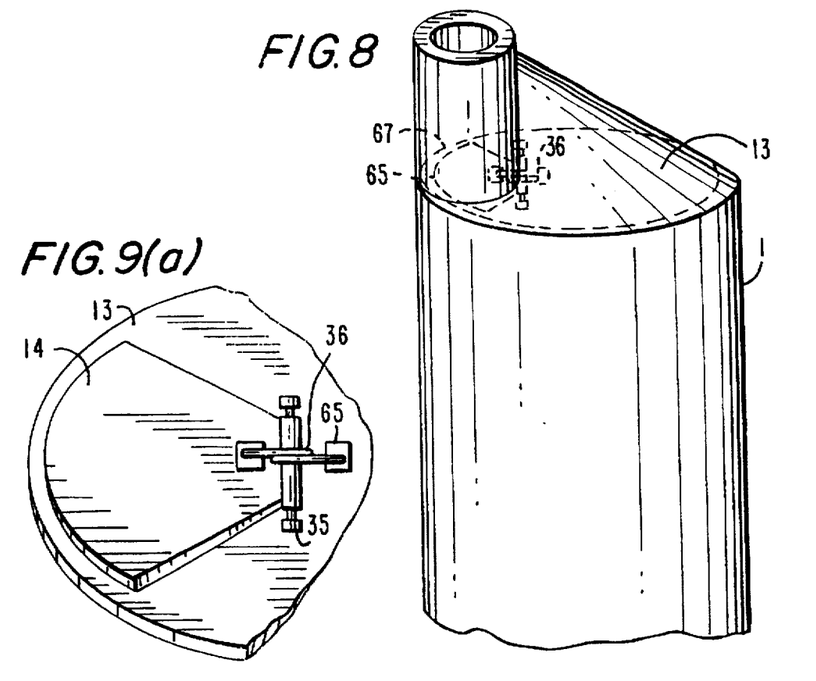
FIG. 8 is a side perspective view of the distal end of the housing with the laparoscopic instrument contained therein in a retracted position.
Figure 9B:
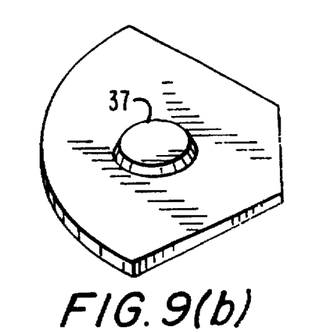
FIG. 9 is a top and bottom perspective view of a preferred embodiment of a valve plate assembly for the laparoscopic instrument assembly of FIGS. 1(a)–(c).
Figure 10A:
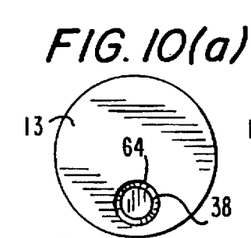
FIG. 10(a) is a bottom plan view of the front plate with valve plate assembly removed.
Figure 10B:
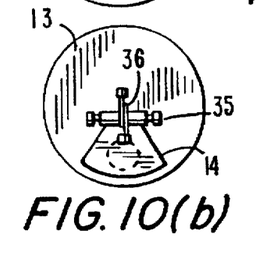
FIG. 10(b) is a bottom plan view of the front plate with valve plate assembly attached.
Figure 10C:
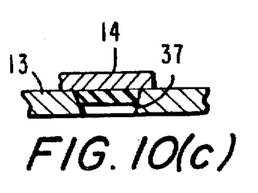
FIG. 10(c) is a side cross-sectional view of front plate with valve plate assembly attached as in FIG. 10(b).

The front plate assembly and the valve cap are explained in additional detail at the discussion relating to FIGS. 8–10, infra.

Figures 3A, 3B, 4A, 4B, 4C, 4D, 4E:
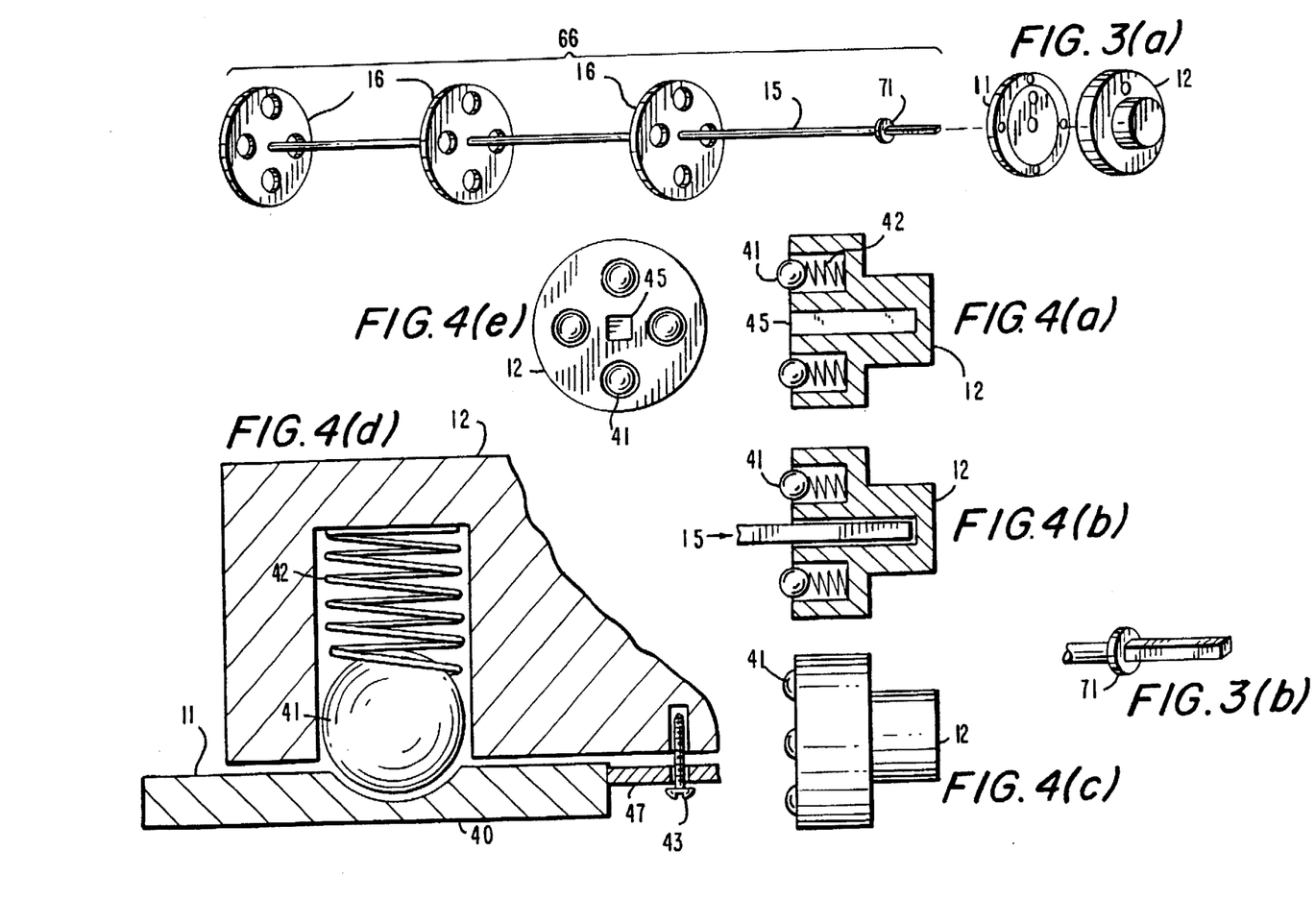
FIG. 3(a) is an exploded side elevational view of a preferred embodiment of a guide disk assembly for the laparoscopic instrument assembly of FIGS. 1(a)–(c).
FIG. 3(b) is an enlarged side elevational view of the proximal end of the center post for the guide disk assembly as shown in FIG. 3(a).
FIG. 4(a) is a side cross-sectional view of a preferred embodiment of a selector knob in its operational state not attached to the center post.
FIG. 4(b) is a side cross-section view of the selector knob in its operational state attached to the center post.
FIG. 4(c) is a side elevational view of the selector knob of FIGS. 4(a) and 4(b).
FIG. 4(d) is a enlarged cross sectional view of the ball bearing assembly of the selector knob of FIGS. 4(a)–(c).
FIG. 4(e) is a bottom view of the selection knob of FIG. 4(a).

FIGS. 1(a)–(c) also show selector knob 12 which articulates with center post 15 to rotate guide disk assembly 66 (shown at FIG. 3(a)) within the housing 1.

Figure 2:
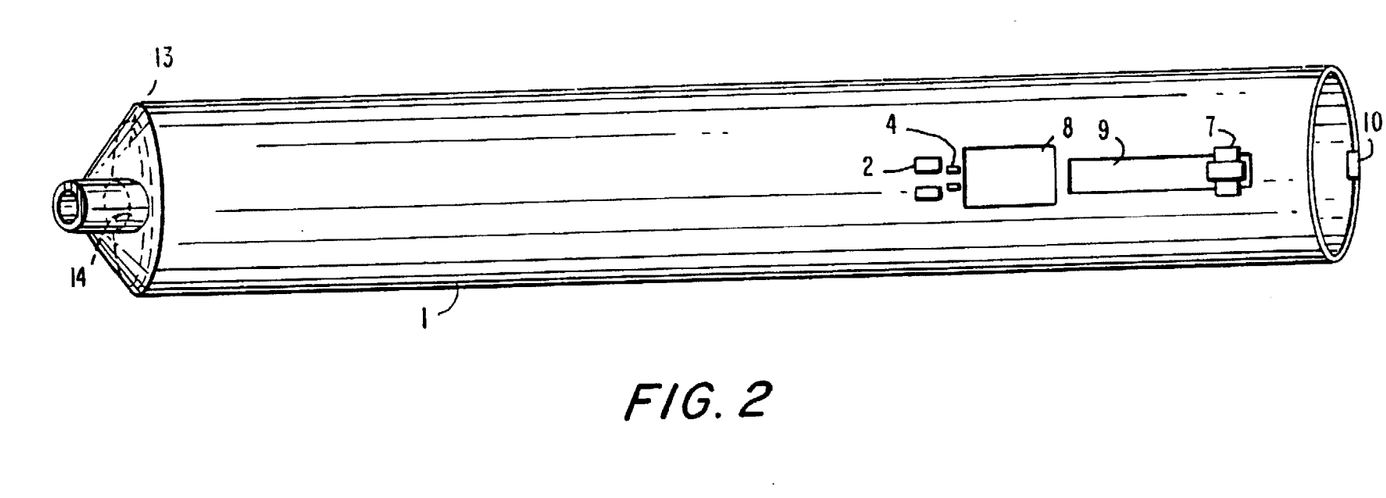
FIG. 2 is a side elevational view of a preferred embodiment of a housing for the laparoscopic instrument assembly of FIGS. 1(a)–(c).

FIG. 2 illustrates a preferred embodiment of a housing 1 for this laparoscopic instrument and certain components fixed to or incorporated into the housing 1. The proximal portion of the housing 1 includes an elongated tubular segment incorporating several components, including latch tab sockets 10, a slider handle 7, a slider track 9, an instrument articulation port 8, the swing arm catch plate 4 and the instrument handle post 2.

In the preferred embodiment, the instrument articulation port 8 has a substantially rectangular opening in the housing 1 of sufficient size to provide access, and thereby facilitate contact, between the articulating gear 29 of the handpiece and the instrument gear grooves 19 of the laparoscopic instrument 18 when the handpiece is in the engaged position and the instrument 18 is in the advanced position.

The selected instrument 18 is advanced and retracted by the slider handle 7 which slides along slider track 9. The slider track 9 includes a substantially rectangular opening in housing 1 elongated in the same direction as the housing. Slider track 9 has length sufficient to allow slider handle 7, upon engagement to the slider handle articulating disk 22 (shown at FIGS. 1(a)–(c)), to advance the laparoscopic instrument 18 from a retracted position, wherein the laparoscopic instrument 18 is housed completely within the housing 1, to an extended position, wherein the laparoscopic instrument extends outside of the housing 1 and is in a position for use during surgery. The slider track 9 has a width appropriate to accommodate the track-engaging portion of the slider handle 7. The slider handle 7 moves along slider track 9 and engages slider handle articulating disk 22 of instrument 18 within the housing 1 for the purpose of advancing and retracting instrument 18 as described above, and can be operated by an operating surgeon from without the housing 1.

Figure 15A:
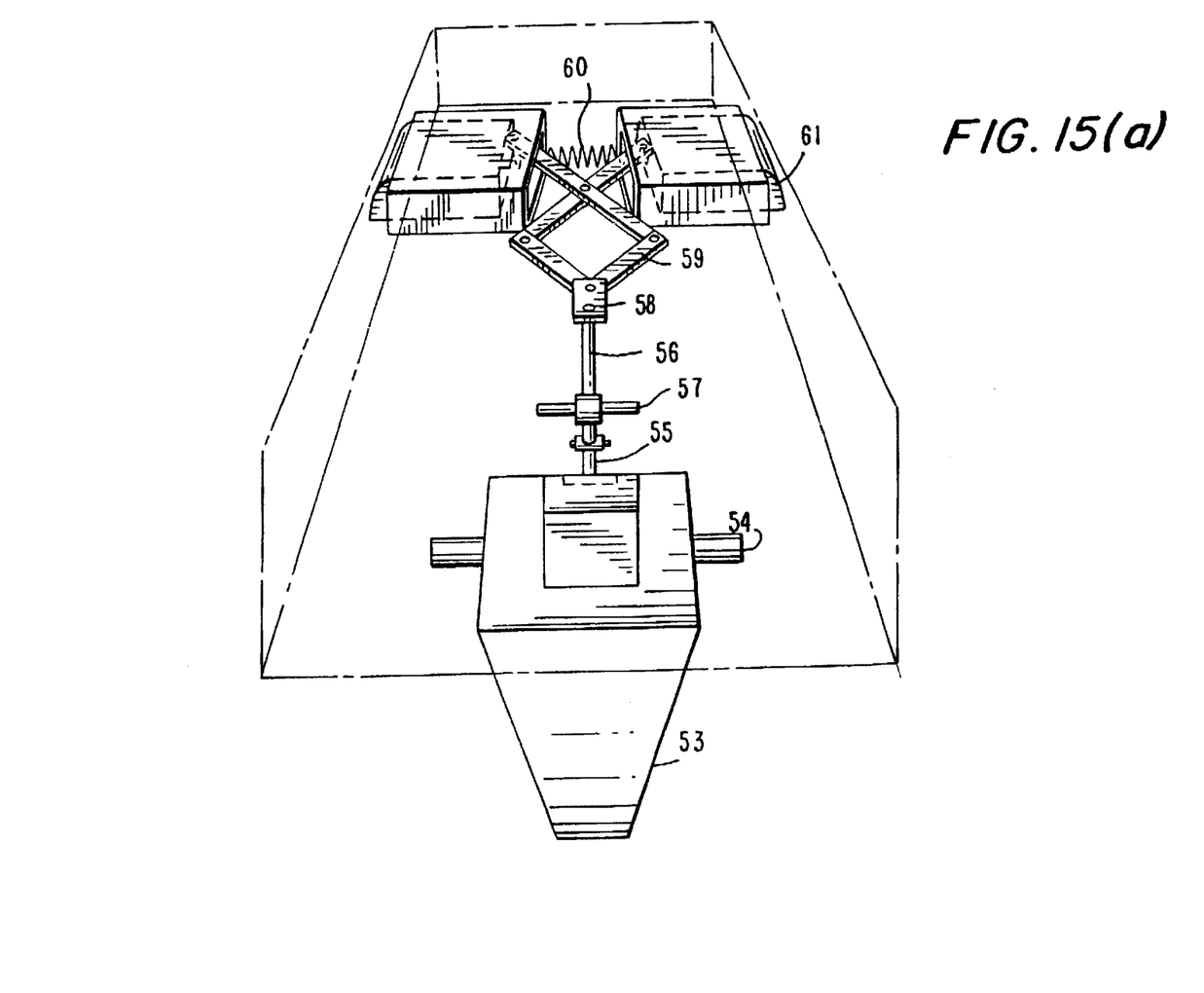
FIG. 15(a) is a top perspective view of a preferred embodiment of a of trigger mechanism for the laparoscopic instrument assembly of FIGS. 1(a)–(c).
Figure 15B:
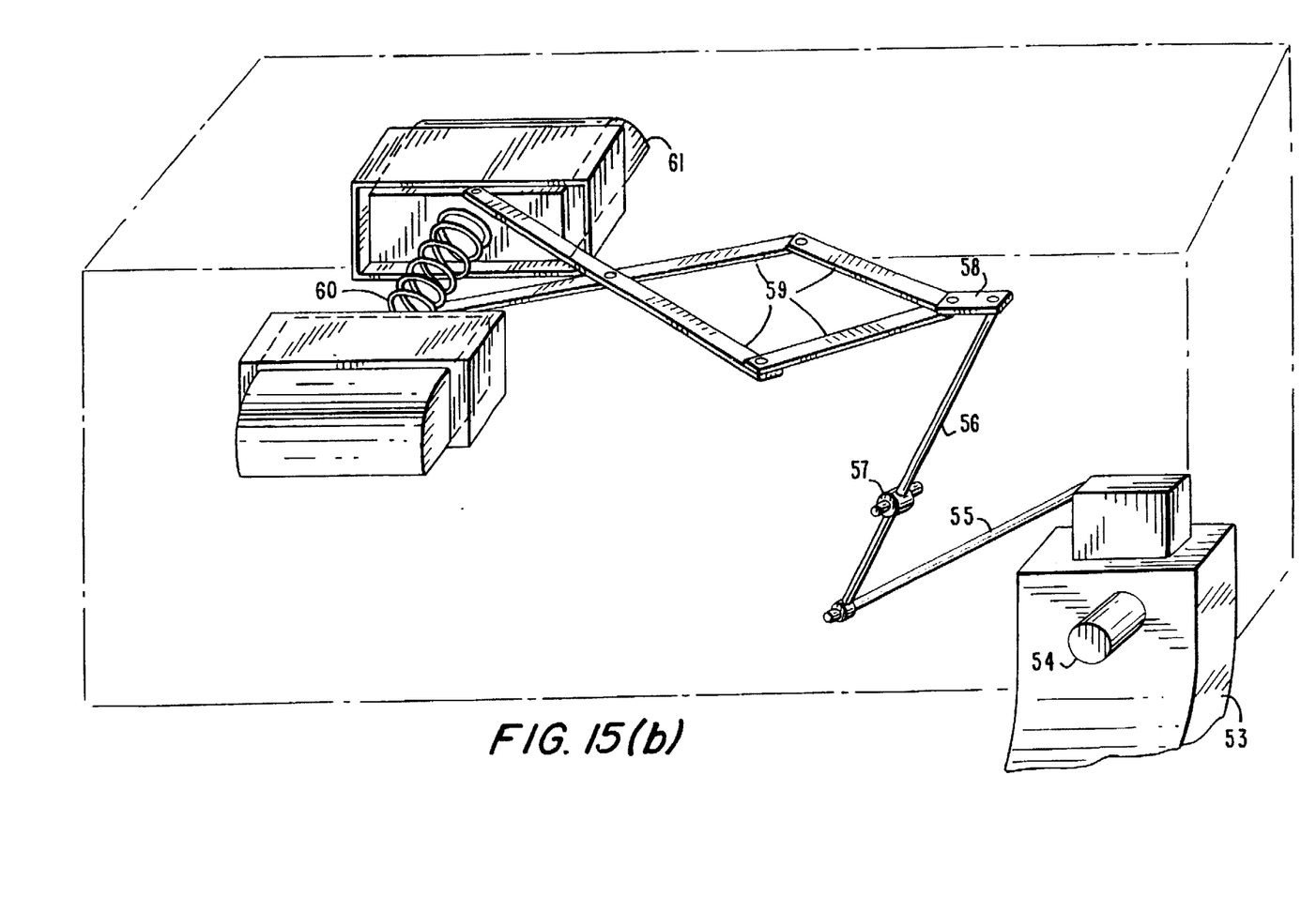
FIG. 15(b) is a side perspective view of the trigger mechanism of FIG. 15(a).

The swing arm catch plate 4 is positioned below the instrument articulation port 8 and allows the articulating handpiece to achieve an engaged position without support of the operating surgeon. The swing arm catch plate 4 provides a raised surface above the outer surface of the housing 1 under which the locking blocks 61 of the trigger mechanism (see FIG. 15 and discussion relating thereto) can secure the handpiece.

The handle post 2 is situated immediately distal to swing arm catch plate 4. Handle post 2 is ideally attached to or incorporated into the outside of the housing 1 and provides pivot support for the second handle 5 via instrument handle pivot point 24 (shown at FIGS. 11(a) and 12).

Figure 6:
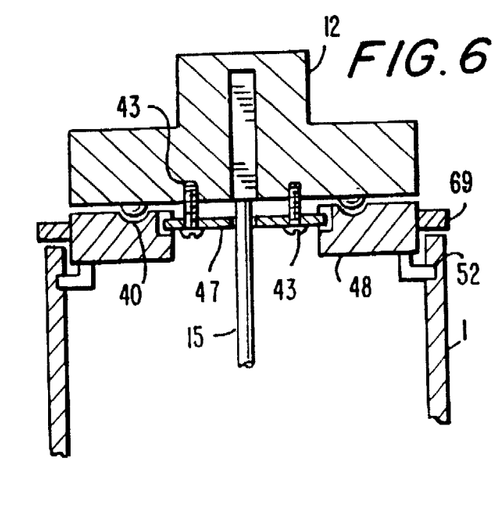
FIG. 6 an enlarged side cross-sectional view of the selector knob and rear plate assemblies of FIGS. 4(a)–(c) and 5(a)–(c).
Figure 7A:
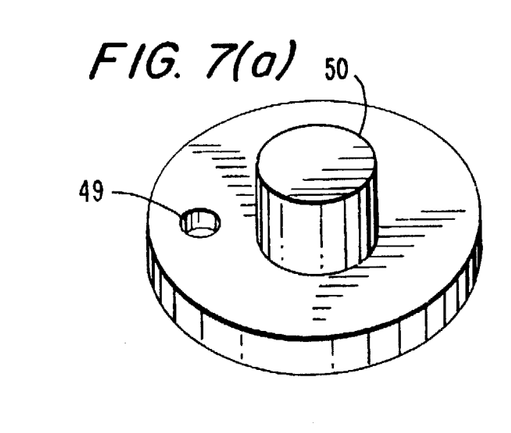
FIG. 7(a) is a top perspective view of the selector knob of FIG. 4(a).
Figure 7B:
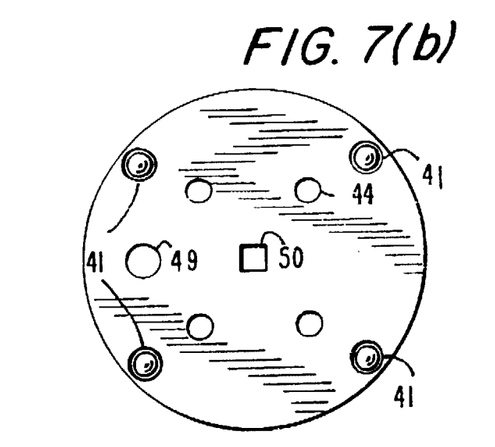
FIG. 7(b) is a bottom plan view of the selector knob of FIGS. 4(a) and 7(a).
Figure 7C:
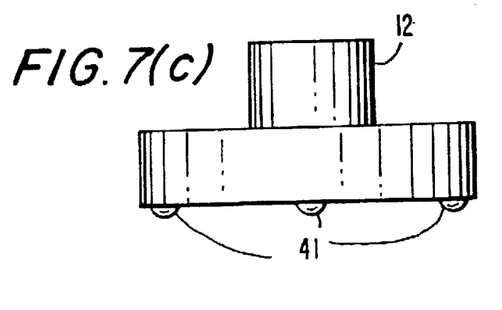
FIG. 7(c) is a side plan view of the selector knob of FIGS. 4(a) and 7(a)–(b).

As shown in FIG. 2, a latch tab socket 10 is located at the proximal end of housing 1 to facilitate attachment and orientation of rear plate assembly 11 (see FIG. 6 and discussion relating thereto). As explained in additional detail infra, rear plate assembly 11, and more specifically, outer disk 48 must be properly oriented with respect to the housing 1 to allow for accurate alignment of the instruments 18, the guide disk assembly 66, the selector knob 12 and related components. To that end, latch tabs 52 located within and extending outward from outer disk 48 engage with latch tab sockets 10 at the proximal end of the inside of housing 1 so that proper orientation of the outer disk 48 is assured when the latch tabs 52 engage the latch tab sockets 10.

FIG. 2 also illustrates the front plate 13 and the valve plate 14 at the distal end of the housing 1. The valve plate 14 includes a disk which forms a barrier at the distal end of housing 1. The valve plate 14 includes an instrument port valve 64 (shown at FIG. 10) which allows for the extension and retraction of a selected instrument 18 through the front plate 13. To maintain airtightness required to achieve the surgical pneumoperitoneum, instrument port valve 64 is covered by valve plate 14, which includes valve stopper 37, when all instruments 18 are retracted. The pneumoperitoneum is maintained by valve membrane 38 when an instrument 18 is extended. These components are explained in greater detail at the discussion relating to FIG. 1, supra, and FIG. 10, infra.

FIG. 3, and more specifically FIG. 3(a), illustrates the guide disk assembly on which the outer shafts 62 of the laparoscopic instruments 18 may be slidably mounted. The rotational position and slidability of instruments 18 relative to the outside of housing 1 of laparoscopic instruments 18 is provided by the guide disk assembly 66. The guide disk assembly 66 is composed of center post 15 to which are permanently attached multiple guide disks 16 and stop guard 71 as one continuous unit. As shown in FIG. 3(b), the center post 15 is squared-off at its proximal end to fit within the square hole 45 of selector knob 12 as shown in FIG. 4(b). Both FIG. 3(a) and 3(b) show a stop guard 71 distal to the squared-off portion, which serves to position inner disk 47.

The entire guide disk assembly 66 is placed into housing 1 with the rear plate assembly 11 detached. The correct degree of insertion of the guide disk assembly within the housing is assured by guide disk stopper 17 at the distal end of housing 1 (see also, discussion relating to FIG. 1, supra)

which assures that the guide disk assembly is inserted into the housing 1 in its properly predetermined position.

Once the guide disk assembly is placed within the housing 1, the laparoscopic instruments 18 may be loaded into housing 1 and mounted in the guide disks 16. Any combination of instruments may be loaded including, but not limited to, scissors, graspers, forceps, dissectors, cautery, suction and irrigation devices etc. Once housing 1 is disposed within the abdomen of the patient guide disks 16 allow rotation of selected instrument 18 into proper alignment within the housing 1 using the selector knob 12.

As is illustrated in FIG. 3(a), the proximal end of center post 15 can be inserted through the center post hole 50 of rear plate assembly 11 and, as best shown in FIG. 4(c), into the selector knob 12.

As is shown in FIGS. 4(b) and 6, the selector knob 12 articulates with the center post 15 via a square hole 45 beginning at the distal surface of the selector knob 12 and extending into the selector knob 12 which fits over the squared-off proximal end of center post 15. This arrangement ensures rotation of selector knob 12 and center post 15 as an integral unit.

As illustrated in FIGS. 4(a)–(e) and 7, the selector knob 12 houses several ball bearings 41 which are spring loaded by means of ball bearing spring 42. These ball bearings 41 are evenly spaced around the circumference of the distal surface of the selector knob 12 to thereby correspond to indexing notches 40 on the proximal surface of outer disk 48 of the rear plate assembly 11. Because the square hole 45 of selector knob 12 is locked onto the squared-off end of center post 15 as described above, rotation of selector knob 12 permits rotation of the entire guide disk assembly within housing 1 and thus allows rotation of instruments 18. The indexing notches 40 and the ball bearings 41 are aligned so that upon engagement of a ball bearing 41 with an indexing notch 40 on outer disk 48 of rear plate assembly 11 (rear plate assembly 11 is described in greater detail at the discussion relating to FIG. 6, infra), slider handle articulating disk 22 of the selected instrument 18 is oriented with respect to slider handle 7 such that the slider handle 7 is poised to advance the slider handle articulating disk 22. Once this orientation is established, the slider handle 7, and thus the slider handle articulating disk 22, can be advanced distally along slider track 9 until the distal end of the selected instrument 18 is outside of the housing 1 and is within the patient's abdomen to be used at the surgeon's discretion.

Figures 5A, 5B, 5C, 5D, 5E, 5F:
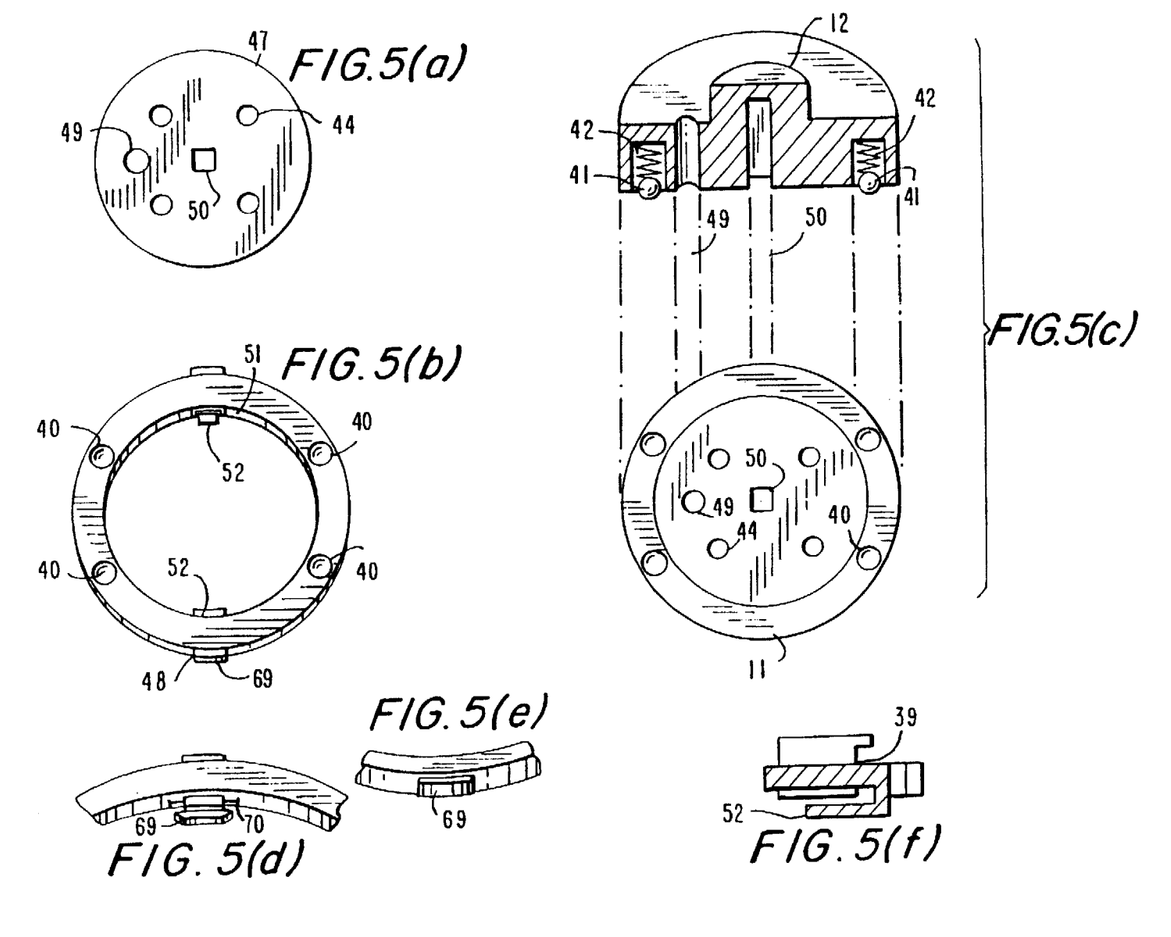
FIG. 5(a) is a top view of a preferred embodiment for the rear plate inner disk for the laparoscopic instrument assembly of FIGS. 1(a)–(c).
FIG. 5(b) is a top elevational view of a preferred embodiment for a rear plate outer disk for the laparoscopic instrument assembly of FIGS. 1(a)–(c).
FIG. 5(c) is an exploded view illustrating assembly of the rear plate inner and outer disks of the rear plate assembly.
FIG. 5(d) is a perspective view of a segment of the rear plate outer disk showing a first view of the latch tab and push tab.
FIG. 5(e) is a perspective view of a segment of the rear plate outer disk showing a second view of the latch tab.
FIG. 5(f) is a partial cross-sectional view of the latch tab and push tab.

The rear plate assembly 11 is illustrated in FIGS. 5(a)–(f) and 6 and includes an inner disk 47 and an outer disk 48. As shown in FIG. 5(a), the inner disk 47 has six holes bored thereinto; namely; a square center post hole 50 allowing the squared-off end of center post 15 to extend outside of the rear plate assembly, instrument extension hole 49 allowing an instrument to extend outside the housing and to be connected to an external piece of equipment, and four screw holes 44 allowing attachment by screws 43 of inner disk 47 to the distal surface of selector knob 12.

As shown in FIG. 5(b) and (c), the outer disk 48 includes indexing notches 40 on its proximal surface spatially corresponding to the ball bearings 41 of the selector knob 12. Moreover, the inner disk 47 fits within outer disk 48 and rotates freely within it along a track 51. Outer disk 48 also includes several slots 39 extending radially from within the outer disk to the outer rim of the outer disk and also extending distantly to the distal surface of the outer disk 48, forming an L-shaped opening within the outer disk 48. Push tab 69 rests within slot 39, extends past the outer rim of outer disk 48, and connects to latch tab 52 through the portion of the slot 39 extending through the distal surface of outer disk 48. Push tab 69 is radially biased away from inner disk 47 by position bands 70.

Once assembled, the rear plate assembly 11 is releasably attached to the outside of housing 1 by latch tabs 52 which are inserted into corresponding latch tab sockets 10 incorporated into the housing 1 thus securing outer disk 48 to housing 1 and ensuring the orientation of the instrument (see FIGS. 3–5 and related discussion of the selector knob, supra) while inner disk 47 is freely rotatable within outer disk 48. In operation, the surgeon may remove the rear plate assembly 11 by inwardly moving push tab 69 towards inner disk 47, thereby also inwardly moving latch tab 52 out of latch tab socket 10. The latch tabs 52 protrude from the outer edge of outer disk 48. These latch tabs 52 are preferably small and square or rectangular in shape, and protrude away from the outer edge of the outer disk no more than a distance equal to or less than the thickness of the wall of the housing 1. The rear plate assembly 11 can be detached before, during or after surgery to allow for the instruments 18 to be changed, cleaned or otherwise manipulated.

FIGS. 8–10 illustrate the distal end of the instrument assembly. Referring specifically to FIG. 8, the front plate 13 includes a circular disk fitted to or incorporated into the distal end of housing 1, its surface substantially perpendicular to the longitudinal axis of housing 1. The front plate 13 is breached by instrument port valve 64 which is covered, in the operational state in which instruments 18 are retracted, by valve plate 14. The valve plate 14 is maintained in position over instrument port valve 64 by a valve plate spring 36. Valve cap 67 is situated over both the front plate 13 and the valve plate 14 and the patient's body during surgery.

Referring specifically to FIG. 10(a), the front plate 13 includes an instrument port valve 64 through which instrument 18 may be advanced and retracted. The instrument port valve 64 surrounds front plate valve membrane 38, which affords a tight seal around the outer shaft 62 of instrument 18 in the instrument's advanced position. This tight seal is critical in maintaining the pneumoperitoneum necessary to perform laparoscopic surgery.

Referring to FIGS. 9 and FIGS. 10(b)–(c), the valve plate assembly includes the valve plate 14, the hinge post 35, the valve plate spring 36 and the valve stopper 37. The valve plate 14 is relatively flat and is of sufficient size to entirely cover the instrument port valve 64. The valve plate 14 is hinged to the front plate 13 by a hinge post 35 and is held in its proper position over instrument port valve 64 by valve plate spring 36. The valve plate spring 36 is fixed to both the front plate 13 and the valve plate 14 by the first and second spring plates 65. The valve stopper 37 is fixed to the surface of valve plate 14 which faces towards front plate 13, and helps to maintain the surgical pneumoperitoneum when instrument 18 is in the retracted position as in FIG. 1(a) by forming an airtight seal at instrument port valve 64.

Upon advancement of the selected instrument 18 by the slider handle 7 along its track 9, the instrument 18 advances through front plate 13. As it advances, valve plate 14 (shown closed) swings open upon its spring loaded hinge post 35 by valve plate spring 36. Those skilled in the art will appreciate that once selected instrument 18 is fully advanced through the front plate 13, the valve membrane 38 ensures maintenance of the pneumoperitoneum affording a tight seal around the selected instrument 18. Once the selected instrument 18 is withdrawn from the abdomen proximally within housing 1, the valve plate 14 will close, given its valve plate spring 36. As shown in FIG. 9, the proximal side of the valve plate 14 incorporates the valve stopper 37 to maintain the pneumoperitoneum in the closed position.

Once the use of the selected instrument 18 is completed the surgeon will disengage the actuating handpiece from the selected instrument 18 by squeezing the trigger 53. The handpiece may now hang freely about the instrument handle pivot point 24 as it did prior to the advancement of selected instrument 18. Using the slider handle 7, the surgeon may slide the selected instrument 18 along the track 9 to the maximum proximal (retracted) position. Once this has been accomplished, the surgeon can use selector knob 12 as previously described to choose any of other instruments 18 mounted within guide disks 16 for use.

FIGS. 11-14 illustrate the components and features of the actuating handpiece for the laparoscopic instrument of the present invention. Referring specifically to FIG. 11(a), second handle 5 is fixed to housing 1 by instrument handle pivot point 24 at handle post 2. There is shown first handle 6 pivotally fixed to second handle 5 at a pivot 25. As shown in FIG. 14, the first handle 6, and more specifically the first handle articulation guide 31, articulates with articulating disk 21. As also shown in FIG. 1(c), this articulation between first handle articulation guide 31 and articulating disk 21 can be achieved only when selected instrument 18 has been advanced to its extended position by slider handle 7 and the handpiece is engaged. Referring again to FIGS. 11(a) and 14, the two prongs of second handle guide 30 at the end of second handle 5 surround instrument gear grooves 19 on two sides without directly contacting instrument gear grooves 19, the purpose of second handle guide 30 being to ensure that instrument articulating gear 29 properly articulates with instrument gear grooves 19. Both first handle articulation guide 31 and second handle guide 30 extend inside the housing 1 through an instrument articulation port 8 (see discussion of FIG. 2).

Referring specifically to FIG. 12, the proper position of first handle 6 with respect to the second handle 5 is maintained by handpiece spring loaded mechanism 34 which pushes against pivot arm 33 of first handle 6. While the first handle 6 is in its neutral position (the spring loaded mechanism 34 being neither compressed nor stretched by the action of the surgeon), the first handle 6 will automatically be poised to articulate with articulating disk 21 of selected instrument 18 upon engagement of the handpiece. The proper position of the second handle 5 and the second handle guide 30 is maintained at all times since it is pivotably fixed to the housing 1. Once the actuating handpiece has articulated with selected instrument 18, the relative action of the second 5 and first handle 6 will allow for the operation actuating of selected instrument 18 at its distal tip.

It should be noted that the second handle 5 has grooves cut into it corresponding to the fingers of the operating surgeon; ergonomically designed for comfort of use and to facilitate placement of said surgeons fingers during an operative procedure.

Figure 11A:
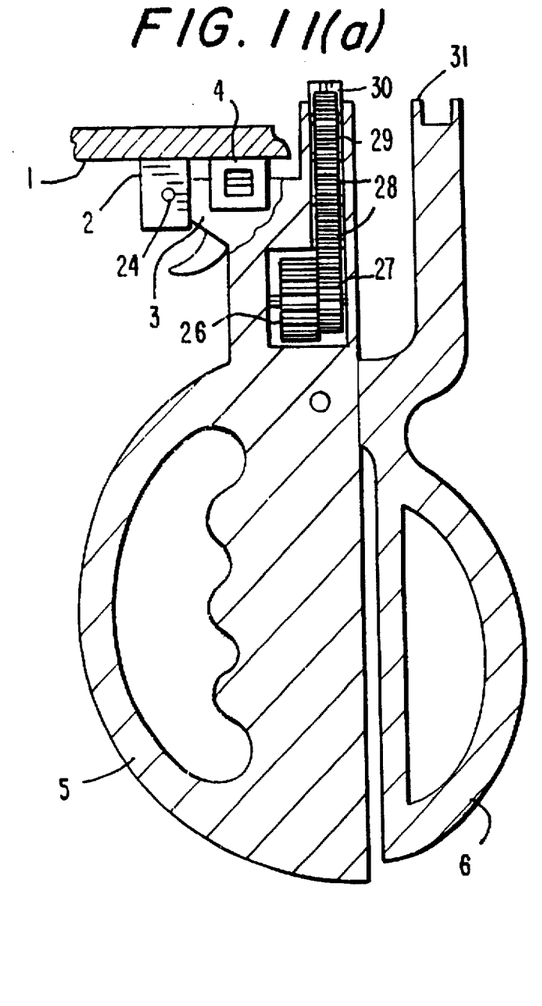
FIG. 11(a) is a side cross sectional view of a preferred embodiment of an actuating handpiece for the laparoscopic instrument assembly of FIGS. 1(a)–(c).
Figure 11B:
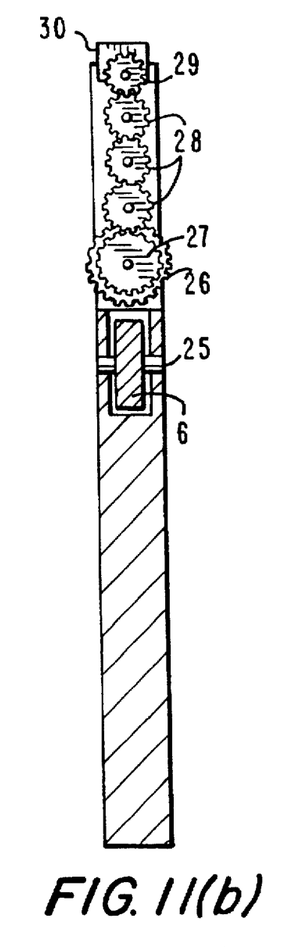
FIG. 11(b) is a top cross-sectional view of the actuating handpiece of FIG. 11(a).

FIGS. 11(a), 11(b) 12, 13 and 14 illustrate the gear linkage between instrument rotating knob 26 and instrument gear grooves 19. As is shown in FIGS. 11(a), 11(b) and 12, instrument rotating knob 26 is positioned in second handle 5 between housing 1 and the pivot 25 and rotates in a plane substantially perpendicular to the longitudinal axis of housing 1. The instrument rotating knob 26 includes a geared portion for articulation with other gears adjacent to a non-geared portion, cross-stretched for articulation with a surgeon's figures. As shown in FIG. 11(b) and FIG. 13, the instrument rotating knob 26 moves rotating knob gear 27 which articulates with one or more intervening gears 28 which rotate in substantially the same plane as the gear portion of the instrument rotating knob 26. In turn, one of the intervening gears 28 articulates with the instrument articulating gear 29. As shown at FIGS. 11(a), 11(b) and 14, the instrument articulating gear 29 in turn articulates with the instrument gear grooves 19. Rotation of instrument gear grooves 19 causes rotation of the entire instrument 18 allowing the operating surgeon to rotate the instrument 18 a full 360° in either direction.

The trigger mechanism by which the handle is captured and released is shown in greater detail in FIGS. 15(a) and (b). FIG. 15(b) shows a side view of the trigger mechanism. A trigger member 53 extends inferiorly and outward from swing arm 3 to allow actuation of this mechanism by the operating surgeon and hinges about pivot bar 54. When the trigger member 53 is pulled this results in action in connecting articulating arms 55 and pivoting articulating arm 56. More specifically, the connecting articulating arm 55 is pushed forwardly resulting in a rearward movement of the pivoting articulating arm 56 about pivot point 57. The pivot point 57 is positioned such that the path of travel of arm 56 at its articulation point with connector bar 58 is maximized. This rearward force applied to the connector bar 58 at its point of connection with articulating arm 56 causes the scissor arms 59 to contract. Contraction of the scissor arms 59 will cause compression of the locking block spring 60 causing inward motion of the locking blocks 61 and in turn release of the actuating handpiece from the swing arm catch plate 4 located on housing 1. Upon release of the trigger member 53, the recoil of locking block spring 60 will push locking blocks 61 to extend beyond the edge of swing arm 3. As a result thereof, the path for locking blocks 61 which is cut into swing arm 3 only allows the striking surface of locking blocks 61 to protrude beyond the edge of swing arm 3. The striking surface of block 61 is cut such that upon hitting strike plate 4 a passive compression of locking block spring 60 will result allowing advancement of second handle 5 toward housing 1. The correct position of the actuating handpiece relative to housing 1 is ensured by the recoil of locking block spring 60 which causes the undersurface of locking blocks 61 to engage a lip of catch plate 4.

By provision of a laparoscopic instrument which incorporates a housing within which are housed a plurality of slidably mounted laparoscopic instruments which can be interchangeably used during an operation without moving a laparoscopic instrument extracorporeally, which includes an actuating handpiece which allows for articulation and rotation of the surgical tip of the laparoscopic instrument and which obviates the necessity of creating multiple incisions for multiple trocar sites, this invention provides a laparoscopic instrument assembly having increased efficiency over instruments common in the art.

By provision of a tubular housing, a guide disk assembly on which to mount laparoscopic instruments, and the means to position, advance and retract these instruments, this invention provides a laparoscopic instrument assembly in which multiple laparoscopic instruments may be effectively housed for use in laparoscopic surgery. Because the instruments in their retracted positions remain within the housing, this invention provides a device which allows individual use of multiple laparoscopic instruments without the need for moving presently unused instruments extracorporeally.

The trigger mechanism of the actuating handpiece allows for uncoupling and subsequent engagement of the actuating handpiece with a succession of laparoscopic instruments. The instrument handle pivot point and swing arm, which attach the handpiece to the housing, allow this uncoupling and engagement to be accomplished without the need for removing either the instrument or the handpiece from the laparoscopic instrument assembly.

The detachable rear plate assembly, latch tabs and latch tab sockets allow for the removal of laparoscopic instruments. These components work in conjunction with the front plate assembly, which maintains the pneumoperitoneum even when the rear plate assembly is removed, in providing a laparoscopic instrument assembly in which one or more laparoscopic instruments may be removed from or added to the assembly, before, during or after surgery. The rear plate assembly instrument extension hole permits use of a device by allowing it to pass through the rear plate while allowing said device to move freely within the housing and to be connected to an external piece of equipment.

The actuating handpiece's instrument rotating knob, the intervening gears, the articulating gear and the instrument gear grooves achieve an actuating instrument which allows for rotational motion of the instrument. The surgeon can operate this system of gears with the same hand that is operating the actuating handpiece without the need for the surgeon to remove his hand from the actuating handpiece.

While the present invention has been particularly shown an described with reference to a preferred embodiment, it will be readily apparent to those of ordinary skill in the art that various changes and modification may be made therein without departing from the spirit and scope of the invention. It is intended that the appended claims be interpreted as including the foregoing as well as various other such changes and modification.

What is claimed is:

1. A laparoscopic instrument assembly comprising:

a housing having a distal end portion, an exterior and an outer diameter smaller than an inner diameter of a laparoscopic cannula, whereby the distal end portion of the housing may be inserted into an abdomen of a patient through the cannula;

a plurality of laparoscopic instruments having surgical tips, said instruments slidably mounted within said housing;

means partially within said housing for positioning a selected one of said plurality of laparoscopic instruments for use during surgery;

actuator means fixed directly to said exterior of said housing and detachably fixed to the selected instrument, for operating said instrument;

rotation means connected to said selected instrument for rotating a tip of said selected instrument about its axis;

means for advancing and retracting said selected laparoscopic instrument;

first sealing means within said housing for maintaining the surgical pneumoperitoneum when said selected instrument is in a retracted position;

second sealing means within said housing for maintaining the surgical pneumoperitoneum when said selected laparoscopic instrument is in an advanced position; and, means adjacent said housing for permitting the removal and insertion one or more laparoscopic instruments from the assembly.

2. The assembly of claim 1, wherein said means for selecting said laparoscopic instrument comprises a center post connected to guide disks and a selector knob.

3. The assembly of claim 2, wherein said laparoscopic instruments are slidably mounted on said guide disks.

4. The assembly of claim 1, wherein said actuator means includes a first handle pivotally fixed to a second handle which is larger than the first handle.

5. The assembly of claim 1, wherein said rotation means comprises an instrument rotating knob mechanically linked to said selected laparoscopic instrument.

6. The assembly of claim 1, wherein said rotation means comprises an instrument rotating knob, housed within said actuator means, mechanically linked to said selected laparoscopic instrument, and wherein said instrument rotating knob can be manipulated without the removal of the surgeon's hand from the actuator means.

7. The assembly of claim 4, wherein said actuator means is capable of being disengaged from said selected laparoscopic instrument.

8. The assembly of claim 1, wherein first sealing means includes a stopper within said housing whereby an air tight seal is formed with said housing.

9. The assembly of claim 1, wherein said second sealing means includes a membrane within said housing, whereby said membrane forms an airtight seal between said housing and said instrument.

10. The assembly of claim 1, wherein said means for advancing and retracting said selected laparoscopic instrument comprises a slider handle cooperating with a slider track.

11. A laparoscopic instrument assembly comprising:

a rigid housing having a distal end portion and an outer diameter smaller than an inner diameter of a laparoscopic cannula, whereby the distal end portion of the housing may be inserted into a abdomen of a patient through the cannula;

a guide disk assembly comprising a center post and a plurality of guide disks rotationally mounted within said housing;

a plurality of laparoscopic instruments slidably mounted on said guide disks;

means for rotating said guide disk assembly, whereby one of said laparoscopic instruments is selected for surgical use;

a slider handle detachably connected to one of said plurality of laparoscopic instruments for advancing and retracting said selected laparoscopic instrument to and from a surgical position;

an actuator comprising a handle pivotably fixed to said housing and detachably fixed to said selected laparoscopic instrument for operating said selected instrument;

an instrument selector knob connected to said center post;

a membrane between said housing and said selected laparoscopic instrument, wherein said membrane is capable of forming an airtight seal between said housing and said instrument, whereby the surgical pneumoperitoneum is maintained; and contamination of the surgical site is prevented;

a stopper within said housing whereby said stopper is capable of forming an airtight seal within said housing, whereby the surgical pneumoperitoneum is maintained and contamination of the surgical site is prevented;

a detachable back plate assembly, wherein one or more laparoscopic instruments can be inserted into or removed from said laparoscopic instrument assembly where the back plate is detachable; and an instrument rotating knob mechanically linked to said selected laparoscopic instrument.

* * * * *